(12) United States Patent
Roy et al.

(10) Patent No.: US 9,695,411 B2
(45) Date of Patent: Jul. 4, 2017

(54) POLYNUCLEOTIDE FOR RECOMBINANT EXPRESSION OF ISOMALTULOSE SYNTHASE

(71) Applicant: Petiva Private Limited, Hyderabad, Telangana (IN)

(72) Inventors: Samir Kumar Roy, Telangana (IN); Saravanakumar Iyappan, Telangana (IN); Saju Varghese, Telangana (IN); Aparna Devi Addala, Telangana (IN); Milky Agarwal, Telangana (IN); Kanumuru Rahul Raju, Telangana (IN); Banibrata Pandey, Telangana (IN)

(73) Assignee: Petiva Private Limited, Hyderabad, Telangana (IN)

( * ) Notice: Subject to any disclaimer, the term of this patent is extended or adjusted under 35 U.S.C. 154(b) by 0 days.

(21) Appl. No.: 14/655,035

(22) PCT Filed: Apr. 17, 2013

(86) PCT No.: PCT/IB2013/053039
§ 371 (c)(1),
(2) Date: Jun. 23, 2015

(87) PCT Pub. No.: WO2013/156940
PCT Pub. Date: Oct. 24, 2013

(65) Prior Publication Data
US 2015/0344865 A1    Dec. 3, 2015

(30) Foreign Application Priority Data

Apr. 17, 2012 (IN) .......................... 1538/CHE/2012

(51) Int. Cl.
*C12N 9/90* (2006.01)
*C12P 19/24* (2006.01)
*C12P 19/12* (2006.01)

(52) U.S. Cl.
CPC .............. *C12N 9/90* (2013.01); *C12P 19/12* (2013.01); *C12P 19/24* (2013.01); *C12Y 504/99011* (2013.01)

(58) Field of Classification Search
None
See application file for complete search history.

(56) References Cited

U.S. PATENT DOCUMENTS

2005/0019852 A1 * 1/2005 Cheng ..................... C12P 23/00
                                                          435/67
2014/0068817 A1 * 3/2014 Dittmar .............. C12N 15/8261
                                                          800/290

FOREIGN PATENT DOCUMENTS

| CN | 101906430 A | 12/2010 |
| CN | 102199611 A | 9/2011 |
| WO | WO9520047 A2 | 7/1995 |
| WO | WO0218603 A1 | 3/2002 |
| WO | WO03061603 A2 | 7/2003 |
| WO | WO 2010068413 A1 * | 6/2010 ........... C07K 14/295 |

OTHER PUBLICATIONS

Merriam-Webster online dictionary definition of "represent", last viewed on Nov. 23, 2010, 1 page.*
PET System Manual, 8th Edition, Novagen, Feb. 1999.*
Nagai et al., Characterization of alpha-glucosyltransferase from Pseudomonas mesoacidophila MX-45, Biosci Biotechnol Biochem. Oct. 1994;58(10):1789-1793.
Ravaud et al., Towards the three-dimensional structure of a sucrose isomerase from Pseudomonas mesoacidophila MX-45, Biologia, Bratislava, 60/Suppl. 16: 89-95, 2005.
Watzlawick et al., Gene Cloning, Protein Characterization, and Alteration of Product Selectivity for the Trehalulose Hydrolase and Trehalulose Synthase from "Pseudomonas mesoacidophila" MX-45• †, Appl Environ Microbiol. Nov. 2009; 75(22): 7026-7036.
Wu et al., Characterization of Pantoea dispersa UQ68J: producer of a highly efficient sucrose isomerase for isomaltulose biosynthesis, J Appl Microbiol. 2004;97(1):93-103.
Wu et al., Characterization of the Highly Efficient Sucrose Isomerase from Pantoea dispersa UQ68J and Cloning of the Sucrose Isomerase Gene, Appl Environ Microbiol. Mar. 2005;71(3):1581-1590.

* cited by examiner

*Primary Examiner* — David J Steadman
(74) *Attorney, Agent, or Firm* — Glenn J. Foulds; Bret E. Field; Bozicevic, Field & Francis LLP

(57) ABSTRACT

The present invention is directed towards genetic modification of native gene encoding for sucrose isomerase and isomaltulose synthase to substantially increase the expression level of these enzymes and use of said enzymes in a process to produce rare disaccharides such as isomaltulose and trehalulose. Also disclosed in the present invention is expression constructs comprising the modified genes and a host cells to express the same.

10 Claims, 14 Drawing Sheets

Figure 1: Schematic view of a gene construct generated for expression of sucrose isomerase in *E. coli*
A
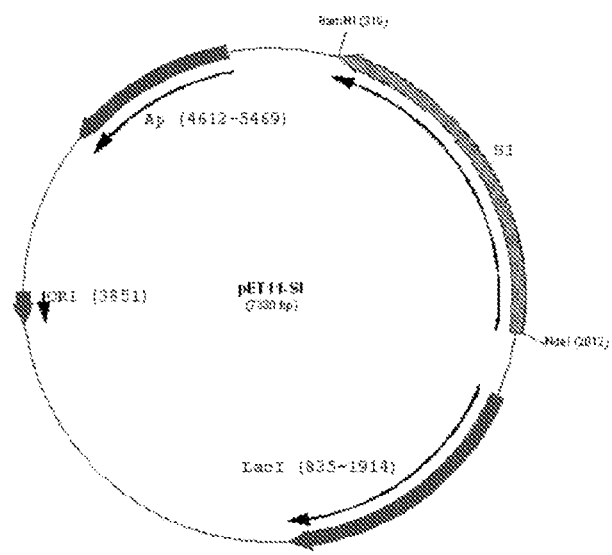
B
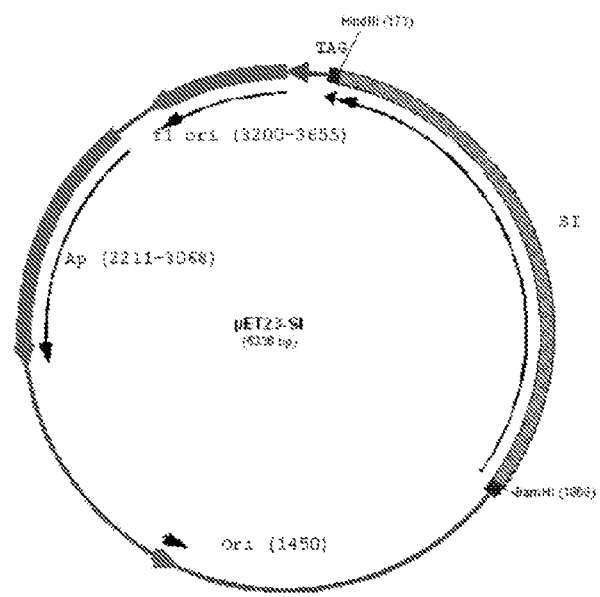

Figure 2: Schematic view of a gene construct generated for expression of isomaltulose synthase in *E. coli*
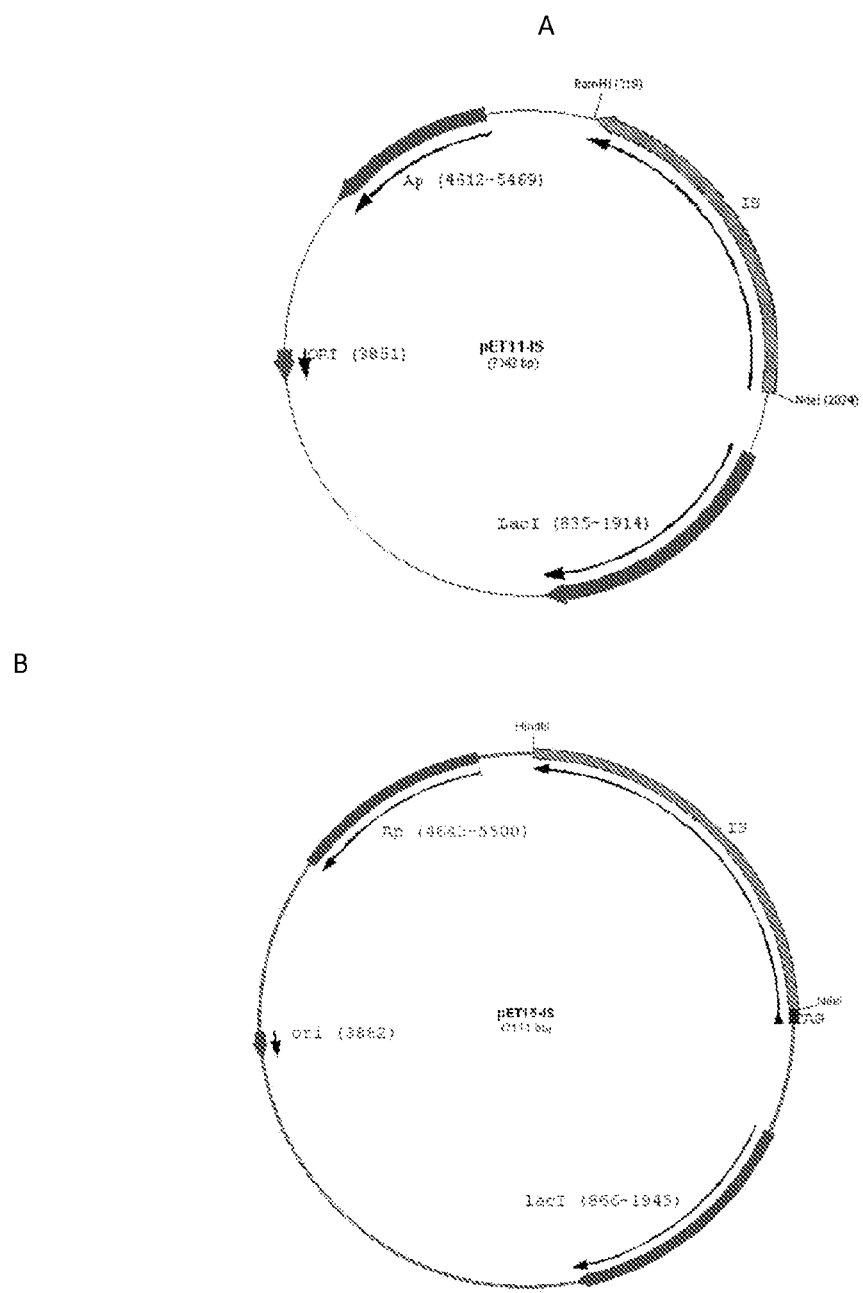

Figure 3: Expression analysis of recombinant sucrose isomerase in *E. coli*.
A
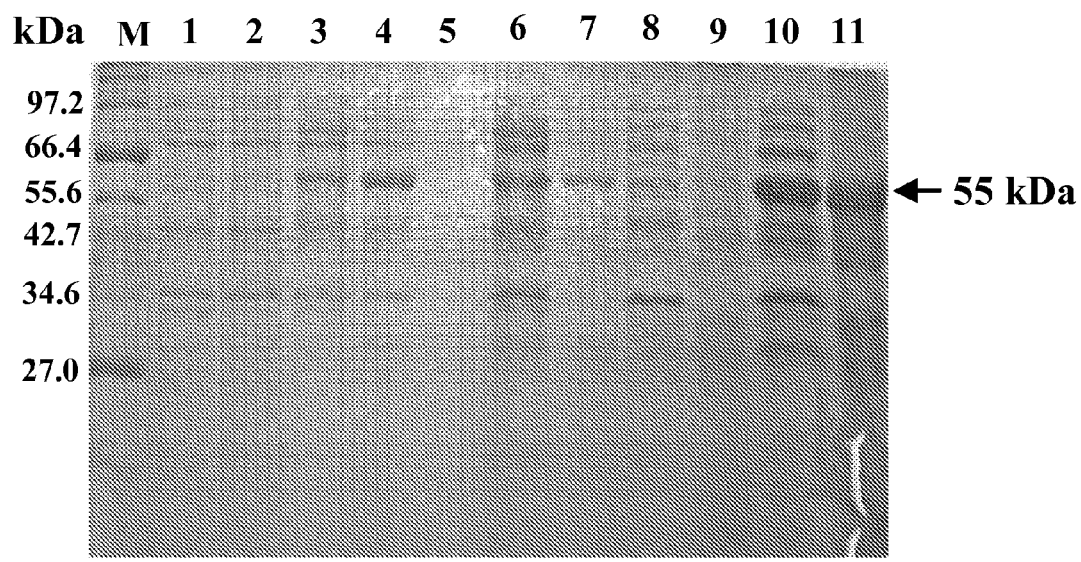
B
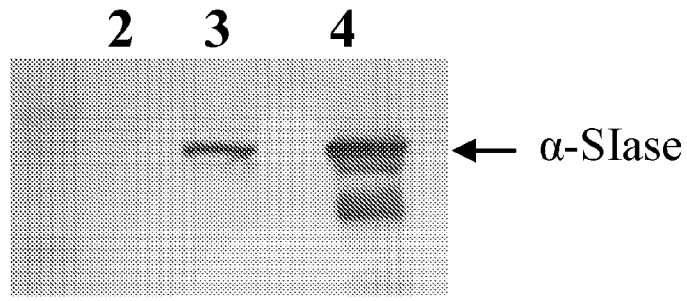

Figure 4: Expression analysis of recombinant isomaltulose synthase in *E. coli*.
A
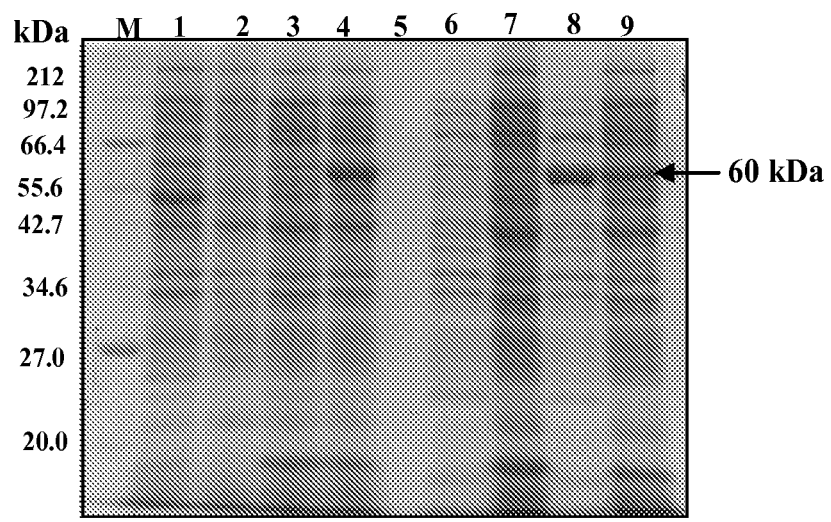
B
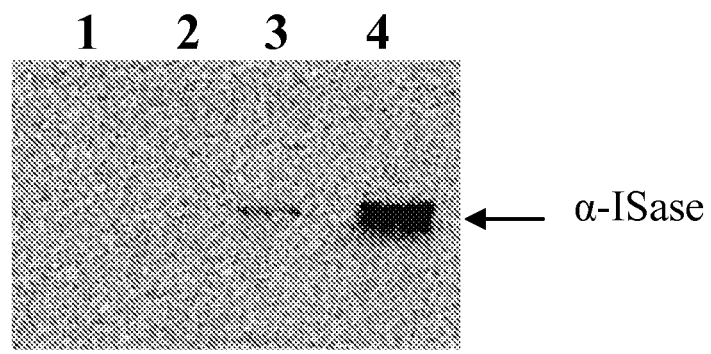

Figure 5: HPLC analysis of recombinant sucrose isomerase activity for substrate to product conversion.
A
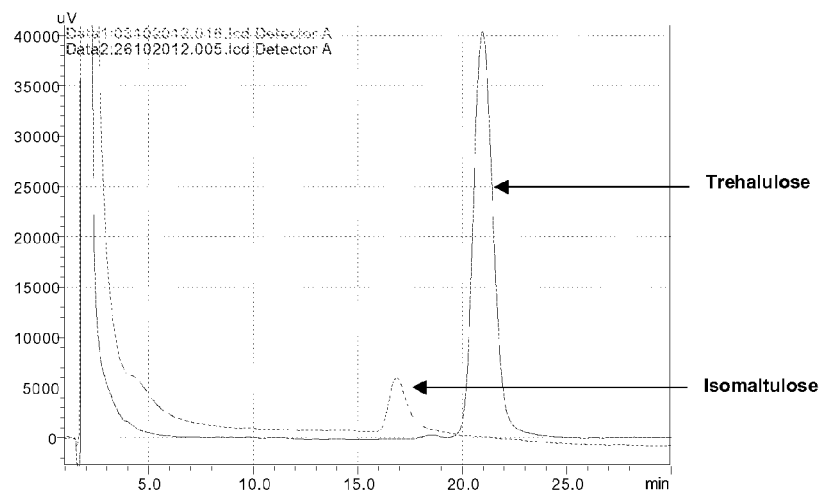
B
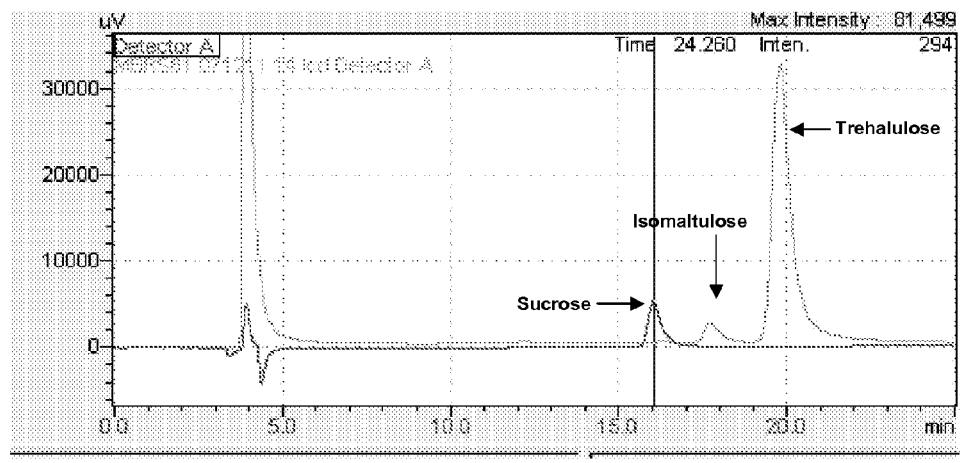

Figure 6: HPLC analysis of recombinant isomaltulose synthase activity for substrate to product conversion.
A
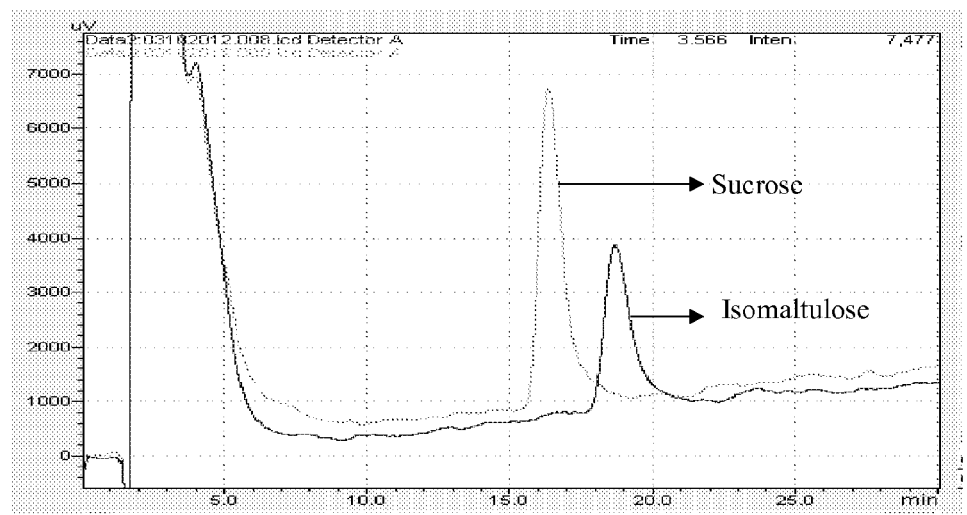
B
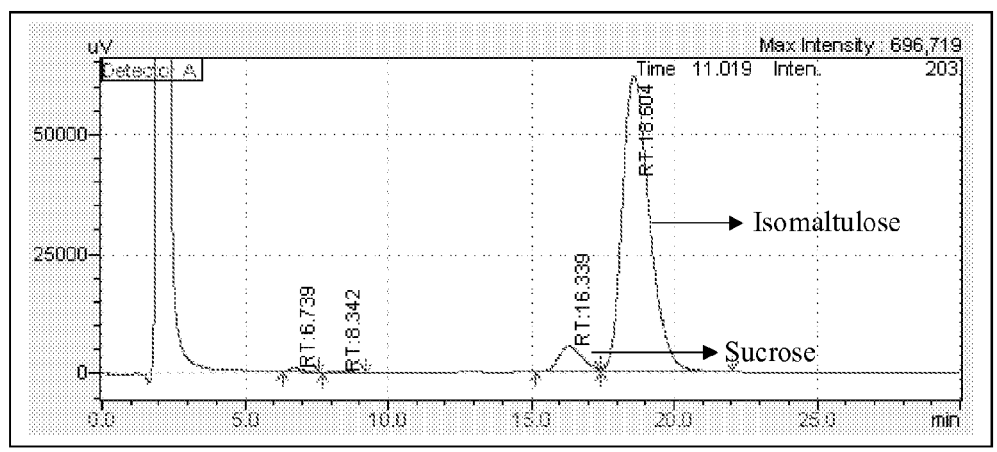

Figure 7: Analysis of purified SIase
A
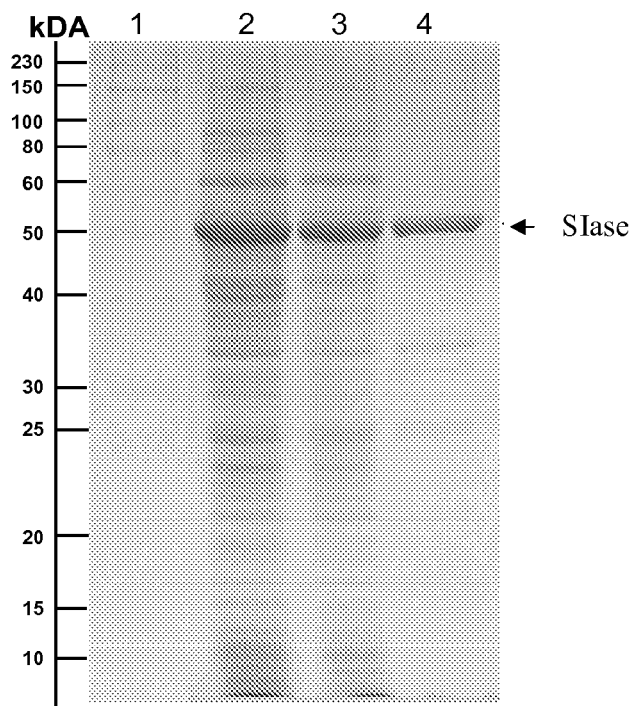
B
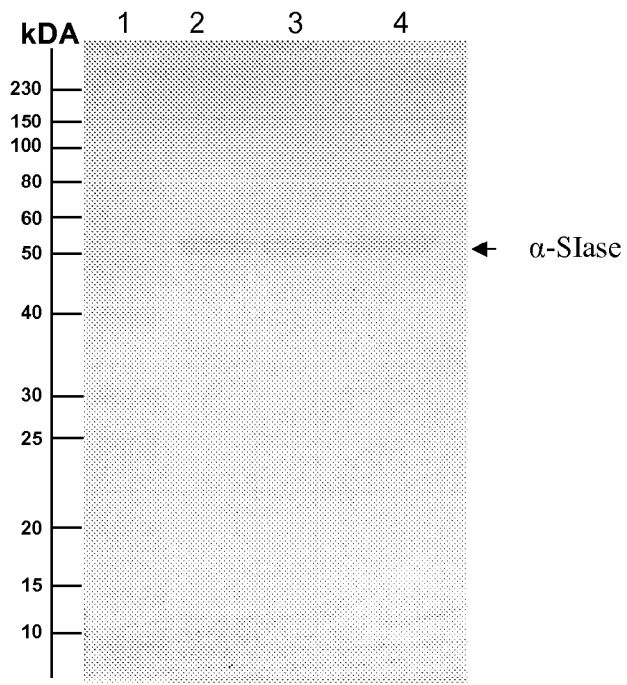

Figure 8: Analysis of purified ISase
A
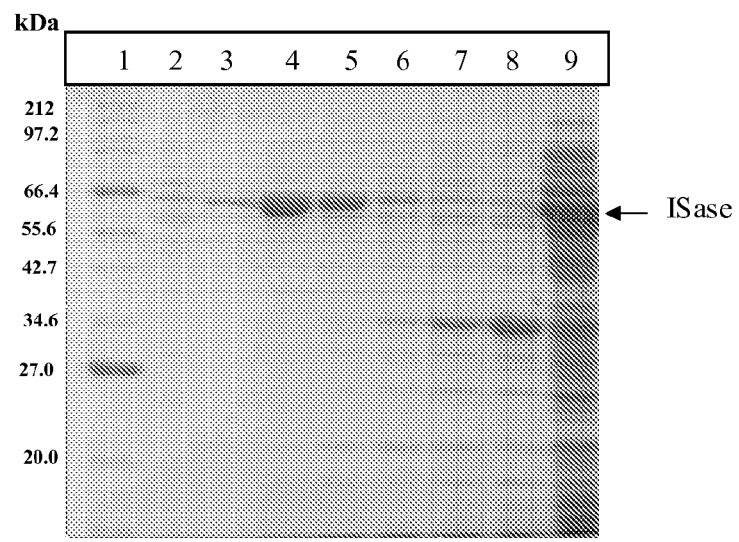
B
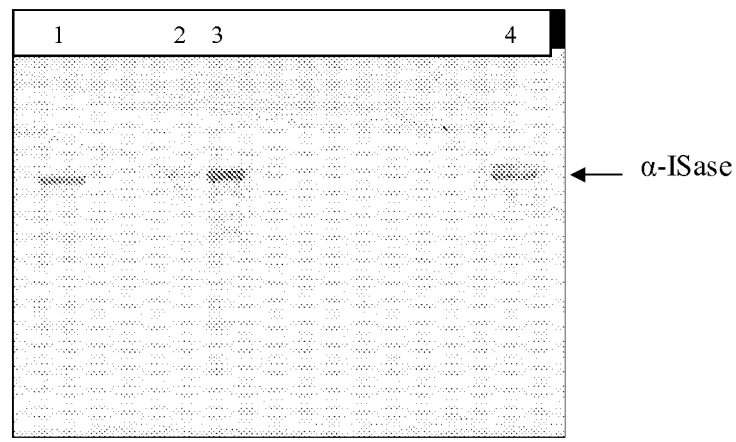

Figure 9: Activity of a sucrose isomerase against reaction pH and reaction temperature
A
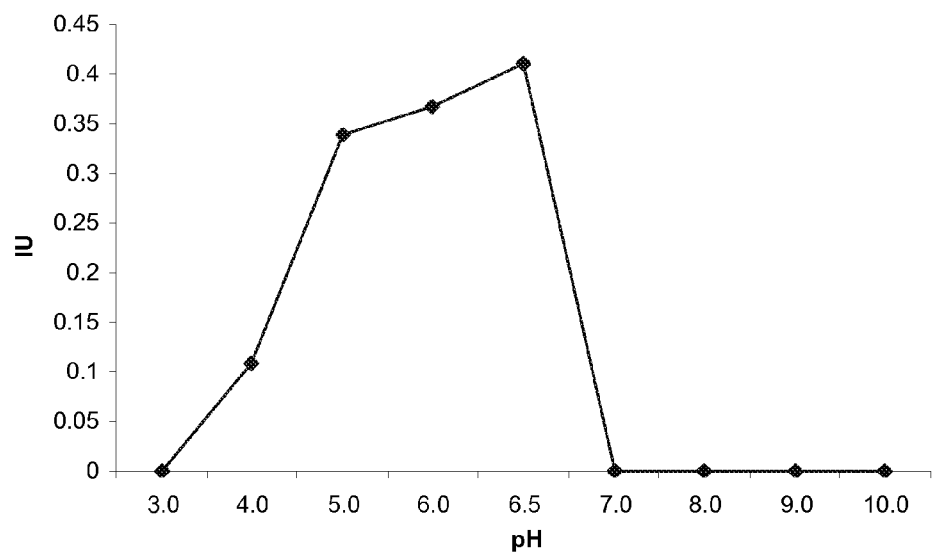
B
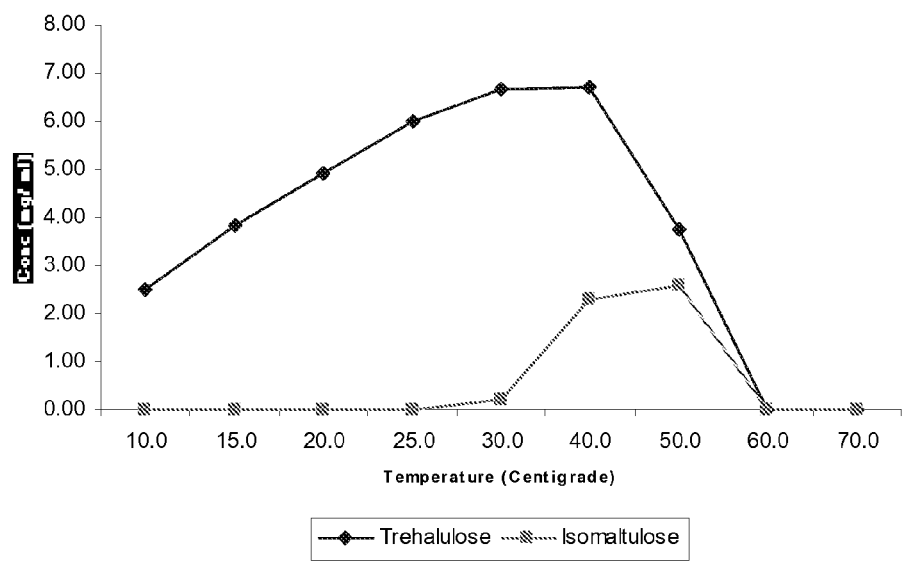

Figure 10: Activity of a isomaltulose synthase against reaction pH and reaction temperature.
A
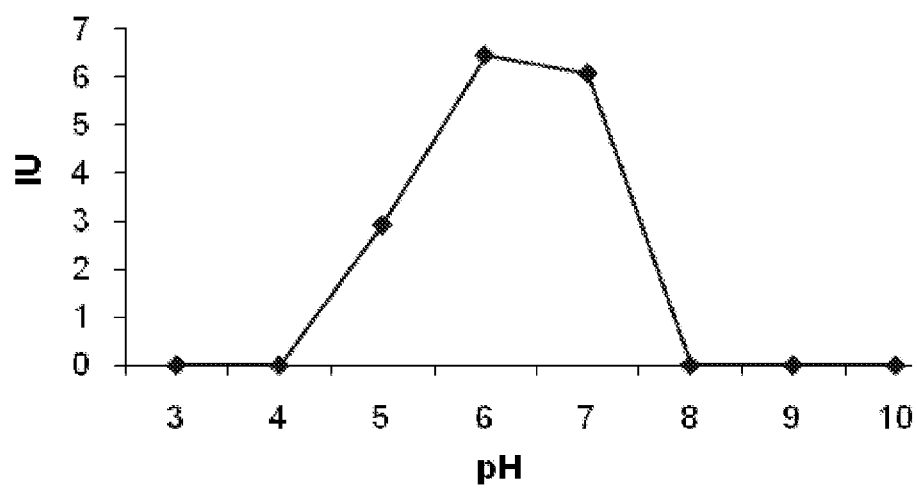
B
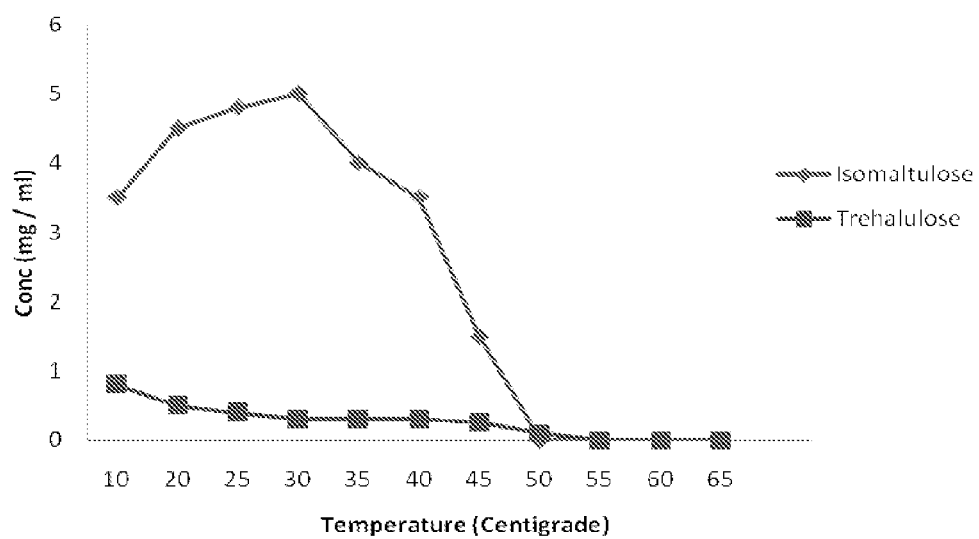

Figure 11: Sequence alignment analysis of modified gene sequence encoding for sucrose isomerase with native gene sequence of *Pseudomonas mesoacidophila* MX45.

```
modified   ------------------------------------------------------------
native     ATGCTTATGAAGAGATTATTCGCGGCGTCTCTGATGCTTGCTTTTTCAAGCGTCTCCTCT  60 modified   ---ATG---GAAGAAGCCGTCAAACCGGGTGCTCCGTGGTGGAAATCGGCAGTGTTTTAT  54
native     GTGAGGGCTGAGGAGGCCGTAAAGCCGGCGCGCCATGGTGGAAAAGTGCTGTCTTCTAT  120
              *  ..***..*** ..*****. .. *** modified   CAAGTCTATCCGCGTCATTCAAAGATACGAATGGTGATGGCATTGGTGATTTTAAAGGT  114
native     CGGGTCTATCCGCGTCGTTCAAGGATACCAACGGTGATGGATCGCCATTTCAAGGCA   180
           **.***********.**.*****.******.**.*********.*****.*****.

modified   CTGACCGAAAAACTGGATTATCTGAAAGGCCTGGGTATCGATGCCATTTGGATCAACCCG  174
native     CTGACGGAGAAGCTCGACTATCTCAAGGGGCTCGGCATAGACGCCATCTGGATCAATCCA  240
           ***** ** .** ** ** ***** ** ** ** **.** **.**** ******.** *.

modified   CATTACGCATCTCCGAACACGGATAATGGCTATGATATTAGTGATTACGCGGAAGTTATG  234
native     CATTACGCGTCTCCCAACACCGATAATGGCTACGATATCAGCGACTATCGAGAGGTCATG  300
           ********.***** ***** *********** **.** *** ***.**.** **.*.

modified   AAAGAATATGGTACCATGGAAGATTTCGATCGTCTGATGGCGGAACTGAAAAAACGTGGC  294
native     AAGGAATATGGCGACGATGCAGGACTTCGATCGTCTGATGGCTGAGTTGAAGAAGCGCGC  360
           ** ********.**.***.**.****.************.**.**** ***.** ** **

modified   ATGCGCCTGATGGTGGATGTCGTTATCAACCATAGCTCTGATCAGCACGAATGGTTTAAA  354
native     ATGCGGCTCATGGTTGATGTCGTGATCAACCATTCGAGTGACCAACACGAATGGTTCAAG  420
           ***** **.*****.******* .*********....***.** ** **********.**.

modified   AGTAGCCGCGGCAGCAAAGATAATCCGTATCGTGATTATTACTTCTGGCGCGATGGCAAA  414
native     AGCAGCCGGCCTCCAAAGACAATCCGTACCGTGACTATTATTTCTGGCGTGACGGCAAA  480
           .*.*..**** **.*.* *****..****** modified   GATGGTCATGAACCGAACAATTACCCGAGCTTTTTCGGCGGTAGCGCGTGGGAAAAAGAT  474
native     GACGGTCATCGAGCCAAACAATTACCCTTCCTTCTTCGGCGGTTCGGCATGGGAGAAGGAC  540
           ** *****.**.** *********...*** *********...** *****.** .**.

modified   CCGGTGACGGGCCAGTATTACCTGCACTATTTTGGTCGCCAGCAGCCCGATCTGAACTGG  534
native     CCCGTAACGGGCAATATTACCTGCATTATTTCCGTCGTCAGCAGCCAGATCTGAACTCG  600
           ... *.******** *  *******.******** modified   GATACCCCGAAACTGCGCGAAGAACTGTACGCCATGCTGCGTTTTTGGCTGGATAAAGGC  594
native     GACACGCCGAAGCTTGCGGAGGAACTCTATGCGATGCTGCGGTTCTGGCTCGACAAGGGC  660
            .***. *** **...****.*  .* modified   GTTAGTGGTATGCGTTTCGATACGGTGGCAACCTATAGCAAAACGCCGGGCTTTCCGGAT  654
native     GTATCAGCTATGCCGTTCGATACGGTGGCTACCTACTCGAAGACACCGGGTTTCCCGGAT  720
           ......***.***********.* .*....***.**** modified   CTGACCCCGGAACAGATCGAAAAACTTCGCCGAAGCATATACCCAGGGTCGGAATCTGCAT  714
native     CTGACACCGGAGCAGATGAAGAACTTCGCGGAGGCCTATACCCAGGGGCCGAACCTTCAT  780
           *****.*****.*********.*.**.**********.********.**.**.*.**

modified   CGTTACCTGCAGGAAATGCATGAAAAAGTTTTCGATCATTACGATGCCGTGACCGCAGGC  774
native     CGTTACCTGCAGGAAATGCACGAGAAGGTCTTCGATCATTATGACGCGGTCACGGCCGGC  840
           ****************....*********......***** modified   AAATTTTTGGTGCGCCGCTGAATCAGGTTCCGCTGTTCATCGATAGCCGTCGCAAAGAA  834
native     GAAATCTTCGCGCGCTCCGCTCAATCAAGTGCGCGTCGTCATCGACAGCCGGAGGAAAGAG  900
           ****.**.*....*....*......*.*.*..........*......**..*..**.*.

modified   CTGGATATGGCGTTTACCTTCGATCTGATTCGTTATGATCGCGGCCTGGATCGTTGGCAC  894
native     CTGGATATGGCTTTCACCTTCGATCTGATCCGTTATGATCGCGCACTGGATCGTTGGCAT  960
           ***********.**.************** ***********.*.************..

modified   CGATCCCGCGCACCGTGGCAGATTTTCGTCAGACCGATTGATAAAGTGGATGCGATCGGC  954
native     ACCATTCCGCGTACCTTAGCGGACTTCCGTCAAACGATCGATAAGGTCGACGCCATCGCG  1020
           ..*...*...***.*...*..***.*..***..*.***.**.**.**..........*.
```

Figure 11 (cont.)

```
modified   GGTGAATACGGTTGGAATACCTTTTTCTTGGGTAACTATGATAATCGGGGTCGTTCT 1014
native     GGCGAATATGGCTGGAACACTGTCTTCCTTGGCAATCACGACAATCCCGTGCGTATCG 1080
           *******.**.********.**.*****.*****.*****.**.**.**.**.

modified   CACTTGGTGATGATCCTGGCAGTGGCGTCAAGTAAGTTCGAAACCCTCGCAACCGTG 1074
native     CATTTTGTGACGATGCTCCGCAATGGCCGAACCCTTGGCGAAGGTCGTCCATCGTC 1140
           ..****.**.*.*****.......***.**** modified   ATGCTGACCTACCGTGGTACCCGGTTTATTTTCCAGCCTATGAACTCGGTATGACCAAT 1134
native     ACCTTGACCTAGCGAGGAACGCCGGTCATCGTTCCAAGGAGATGAACTCGGAATGACCAAC 1200
           **..***********.**.**.*****.**..*****.**.********.**.*****.**.

modified   TATCCGTTTAAAACCGTCAGGATTTCGAGGATATCGAAGTTAAAGTCTTTTCCAGGAT 1194
native     TACCCTTGAAGACGCTGGAGGACTTTGATGATATCGAAGCCAAAGGCTTCGTTCAGGAC 1260
           **.**.**.**.**.*********.**.**************.*****.**.*****.

modified   TACGTGGAAACCGGTAAAGTGACCGGCCGAAGAACTGCTGACGAAGTTGTACTGACCAAC 1254
native     TATGTTCGAAACCGGAAATCCAATCGCNAGGAATTGCTGACGAATGTCGGTTCATACC 1320
           ..***.....*.*.*****....***.* modified   CTGATAATGTCGCTACCCTGTTCAGTGGGATGATGTTCAAATCCGGTCTCACCACG 1314
native     CGCGACAACGCCCGCACGCCCTTCAATGGGATGACAGTCCTAAGCGGGATTCACCAC 1380
           **.**.**.**.******.**.*****.********...***.*******.*****.**.

modified   GGTAAACTGGCTGAAAGCTTAACCGGAATTATACGGAAATTAACGTCGGCTCGAAAC 1374
native     GGCAAACCCTTGCTAAAGGTCAATGCAATGTACACTCAGATCAATCCGTGCGGCAAATT 1440
           **.**.**.*****.**.**.**.**.**.**.**.**.*****.**.**.*****.

modified   GCGATCCGAAATCTGTGTATAGTTTTACCGCAATCGATTAGCATCCGTCATGAAACC 1434
native     GGTCATCTTAAATCGGTGTACACGCTTTACCGCAACCTGACTTGAATCCGGTATGAAACT 1500
           ********.**....**......****.*.....*.****....*...*....****...

modified   CTAGTACGAACGACCGTTCTATCTGATATGATCGGACGAACGGATCTGTACGC 1494
native     CCCGTCGTTCGACCGGGAGCTATCGCGACATCGATCGGACTAAGGCGATGTCTATGC 1560
           ......*....*...***...*.**** modified   TATACCGCTTCTTAGGATCGTGAAACCTACCTGTGCTTCTGAATTTTAAATACAACCG 1554
native     TATATCCGCAGTCAAGATAGTCGAGACCTATCTGGTCGACTCAACTTCAAGGCAGAGGCA 1620
           **.*****....*****.**.*****.*****.**.**.**.**.*****.**.

modified   CCTAGTTTACCCTGCCGGATGGTATGCATATTGTGGAAACCCTGATCGATCTAGTAGC 1614
native     AGGAGTTTCAGGTTGCGCACGCATGTATATTCCGGAAACCTTGATCGAGACCAGTCCG 1680
           .*.**.*******.*****.************.************.**....***...

modified   CTAGTACCGCTTGCCGTCGTTGGGTTCGTCGGAACTCTAACCGTCGCAAAGTGGGATT 1674
native     CCGGTAGCTCGGCGCGGGGGCTGCAAGCCTTGAGCTCCAGCCTTGGCAGTCTGCCACG 1740
           **.*****.*******.**.**.**.*****.**.*****.**....**.**.

modified   TACAAGTGAAATAA 1689
native     TACAAGGGAAGTAA 1755
           *****.*****.***
```

Figure 12:
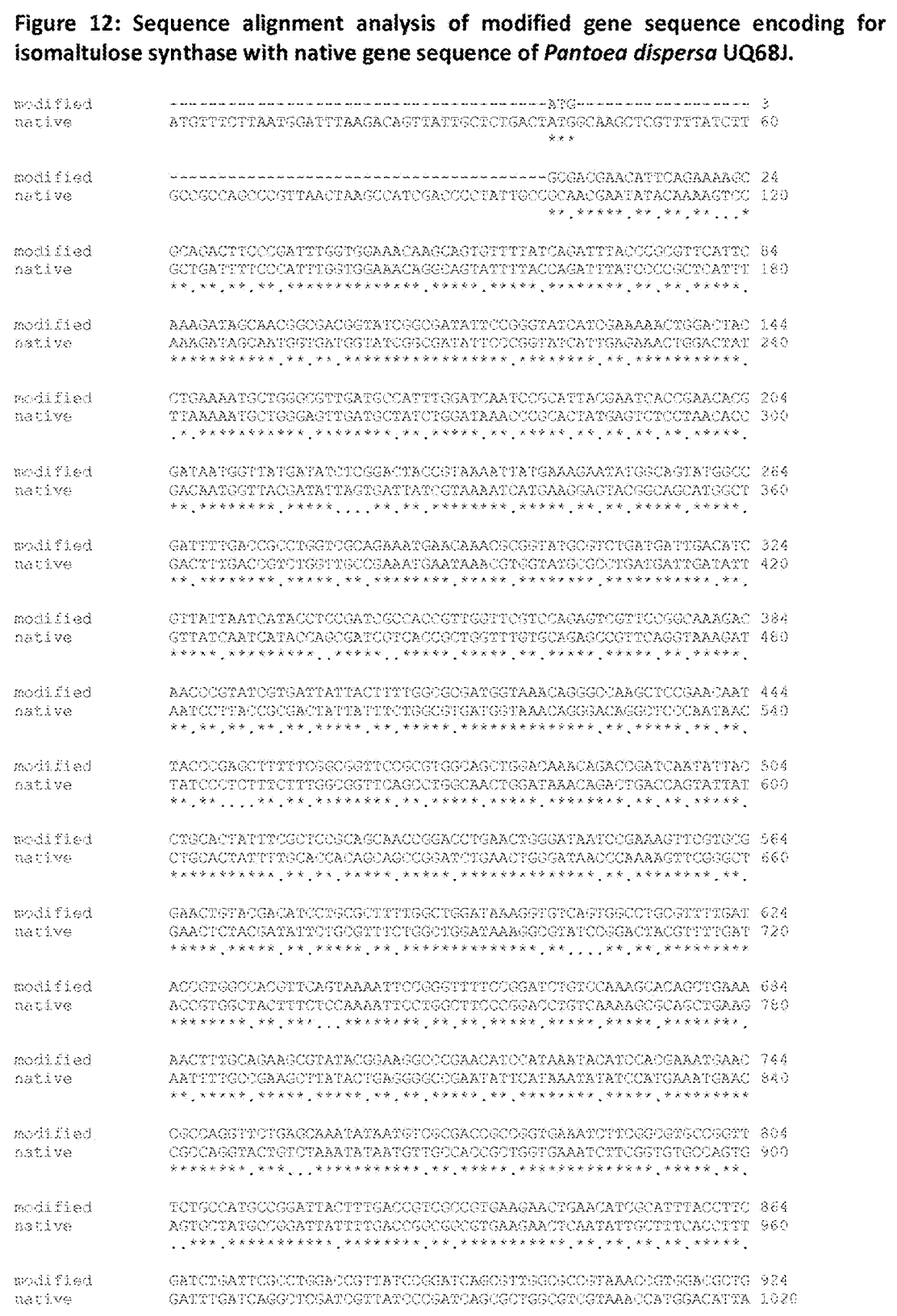

Figure 12: Sequence alignment analysis of modified gene sequence encoding for isomaltulose synthase with native gene sequence of *Pantoea dispersa* UQ68J.

Figure 12 (cont.)

```
                ***.****..*.**.**.********.********.*****.*********.*****...*.
modified        AGCCAGTTCCGTCAAGTCATTTCTCAAACCGATCGCGCGGCCGGTGAATTTGGCTGGAAT  984
native          AGCCAGTTTCGTCAAGTTATCTCTCAGACTGACCGTGCCGCCGTGAATTTGGCTGGAAC  1080
                ********.********.**.*****.**.**.**.**.********************.

modified        GCGTTTTCCTGGATAACCATGACAATCCGCGTCAGCTGTCACACTTTGGTGATGACTCG  1044
native          GCCTTTTCCTTGATAACCATGATAACCGGCGTCAGGTCTCACACTTTGGTGACGACAGC  1140
                **.*******.*********.***.**.*****.*****.************.***...

modified        CCGCAATGGCGCGAACGTBGCGCAAAAGCTCTGGCAACCCTGCTGGTGACGCAGCGTGCT  1104
native          CCACAATGGCGCGGAACGTCGGCAAAAGCACTGGCAACCGCTGCTGCTGACGCAGCGTGCC  1200
                .******.*...***.****.*******.***** modified        ACCCCGTTATTTTCCAGGGTGCGGAACTGGGCATGACGAACTACCCGTTCAAAAACATC  1164
native          ACGCCGTTTATCTTTCAGGGGCGGAGTTGGGAATGACTAATTACCCCTTTAAAAATATA  1260
                **.*******.**.*****.*****..****.*****.**.*****.**.*****.**.

modified        GAAGAATTCGATGACATCGAAGTGAAAGGTTTCTGGAACGATTACGTCGCATCAGGCAAA  1224
native          GAGGAATTTGATGATATTGAGGTTAAAGGCTTCTGAACGACTATGTAGCCAGCGGAAAA  1320
                .*.*....***.****....:..* modified        GTGAATGCAGCTGAATTTCTGCAGGAAGTGCGCATGACGAGCCGTGACAACTCTCGCACC  1284
native          GTAAACGCTGCTGAATTTTTACAGGAGGTTCGCATGACCAGCCGCGATAACAGCGCAACA  1380
                **.**.**:********.*.*****.**.********.*****.**.***:.**.**.

modified        CCGATGCAGTGGAACGATTCCGTTAATGCGCGGTTCACCCAAGCGCAAACCGTCGTTTCAT  1344
native          CCAATGCAGTGGAACGACTCTGTTAATGCGGATTCACCCAGGCGCAAACCCTGGTTTCAC  1440
                .******...****..******.*****.****** modified        CTGAACCCGAATTATAAACAGATTAACGCGGCCGCGAAGTGAATAAACCGGATTCAGTT  1404
native          CTCAATCCCAACTATAAGCAAATCAATGCGCCAGGGAGGGTGAATAAACCGGACTCGGTA  1500
                **.**.**.**.*****.**.**.**.**.***.*.**.***********.**.**.**.

modified        TTCTCGTATTACCGTCAGCTGATCAATCTGCGCCACCAAATTCCGCTCTGACGTCAGGC  1464
native          TTCAGTTACTACCGTCAACTGATCAACCTGCGTCACCAGATCCCGGCACTGACCAGTGGT  1560
                ***...**.********.*******.*****.*****.**.*****.*****...**.

modified        GAATATCGTGATCTGGACCCGCAGAACAATCAAGTTTATGCCTACACCGCATCCTGGAT  1524
native          GAATACCGTGATCTCGATCCGCAGAATAACCAGGTCTATGCCTACACCGTATACTGGAT  1620
                ***.****..******....******.*..****** modified        AACGAAAAATACCTGGTGGTTGTCAACTTCAAACCGGAACAGCTGCATTACGCCCTGCCG  1584
native          AATGAAAAATATCTGGTGGTAGTTAATTTTAAACCTGAGCAGCTGCATTACGCTCTGCCA  1680
                **.********.********..**.**.**.*****.**.************.*****.

modified        GATAACCTGACCATTGCAAGCTCTCTGCTGGAAAATGTGCACCAGCCGTCTCTGCAAGAA  1644
native          GATAATCTGACTATTGCCAGCAGTCTGCTGGAAAATGTCCACCAACCATCACTGCAAGAA  1740
                ***.*.*..************.*....******** modified        AACGCCTCTACGCTGACCCTGGCACCGTGGCAAGCTGGCATTTACAAACTGAATTAA  1698
native          AATGCCTCCAGGCTGACTTCTTGCTCCGTGGCAAGCGGGATCTATAAGCTGAACTGA  1797
                **.*****.*********..**.**.**********.**.**.**.*****....
```

POLYNUCLEOTIDE FOR RECOMBINANT EXPRESSION OF ISOMALTULOSE SYNTHASE

FIELD OF THE INVENTION

The present invention is in the field of biotechnology and more particularly production of rare sugar disaccharides through biological route.

BACKGROUND OF THE INVENTION

Despite their low natural abundance, rare disaccharides hold enormous potential for practical application.

Sucrose (table sugar) is the most widely used sweetener in food production due to its physiochemical and sensorial characteristics, however in recent decades an increased studies on alternative sweeteners is progressing rapidly, since of its high caloric value. Research on the production of oligosaccharides for foods with health benefits was started around late 1970s, and several oligosaccharides such as starch-related, sucrose-related, and lactose-related oligosaccharides have been developed.

Artificial sweeteners also called sugar substitutes were developed in recent years and are used in remarkable amounts instead of sucrose to sweeten foods and beverages but also in drugs and sanitary products. These sweeteners are not decomposed as carbohydrates and are not metabolized like sugars or only fermented slightly by the mouth microflora, which develops an artificial, metallic or licorice-like aftertaste. Therefore they often can be found blended in food to overcome this disadvantage.

Reducing disaccharides such as trehalulose (α-D-glucosylpyranosyl-1,1-D-fructofuranose) and isomaltulose (α-D-glucosylpyranosyl-1,6-Dfructofuranose) are structural isomers of sucrose (α-Dglucosylpyranosyl-1,2-β-D-fructofuranoside) and are naturally present in honey as well as in sugar cane extract in very low quantities. These natural sugars display a sweetening power, bulk, organoleptic and physical properties similar to those of sucrose.

Trehalulose is a non-crystalline saccharide which readily dissolves in water, does not substantially have cariogenicity, and has an about 70% sweetening power of sucrose, it is greatly expected to be used in food products, especially in foods enriched with sweeteners.

Isomaltulose is suitable sucrose replacement, since it's approximately half as sweet as sucrose, and has a similar sweetness quality and has non-carcinogenic properties. Moreover isomaltulose is also used as a raw material for production of another sweetener namely isomalt (palatint) by hydrogenation. Furthermore the reducing property of isomaltulose makes it an attractive industrial precursor for the manufacturing of biosurfactants and biocompatible polymers.

Both disaccharides: isomaltulose and trehalulose can be produced at an industrial scale through isomerization of sucrose using Sucrose Isomerases (Slase) which bio-convert sucrose into both isomaltulose and trehalulose with trace amounts of glucose and fructose.

U.S. Pat. No. 5,336,617 relates to a process for preparing trehalulose and isomaltulose wherein at least the trehalulose-forming enzyme system of a trehalulose-forming microorganism is contacted with a sucrose solution to convert it into trehalulose and isomaltulose in the weight ratio of at least 4:1

Commercial isomaltulose is produced from food grade sucrose through enzymatic isomerisation with sucrose-6-glucosylmutase. In this process the biocatalyst used to convert the sucrose is obtained from non-viable, non-pathogenic P. rubrum (CBS 574.44) cells which were killed using formaldehyde before they are added to the sucrose (U.S. Pat. No. 4,640,894 and U.S. Pat. No. 5,336,617).

The enzymes responsible for bioconversion of sucrose in to its corresponding isomers (Sucrose to isomaltulose or trehalulose) have been reported from different microorganisms such as *Protaminobacter rubrum, Serratia plymuthica, Erwinia rhaponiciti* for isomaltulose production whereas trehalulose producing organisms are *Pseudomonas mesoacidophila* and *Agrobacterium raadiobacter.*

U.S. Pat. No. 4,857,461 discloses the process of extraction of sucrose mutase from periplasmic membranes of *Protaminobacter rubrum* or *Serratia plymuthica* and utilization of same in a radial type bioreactor for the conversion of sucrose to isomaltulose.

In non-patent literature L. Wu et. al., 2004 and 2005 identified a sucrose isomerase from *Pantoea dispersa* UQ68J having isomaltulose synthase activity and expressed in *E. coli*. However the recombinant isomaltulose synthase expressed in *E. coli* carried an additional carboxy-terminal six-His tag and moreover the expression level was low. Similarly, Nagai et al., 1994 showed that sucrose isomerase (also called as trehalulose synthase) activity of the *P mesoacidophila* MX-45. Latter Watzlawick H et. al., 2009 cloned the gene for expression in *E. coli*. However both authors didn't disclose their expression level of sucrose isomerase which is critical for mass production of enzymes at industrial scale.

The mass production of pure trehulose and/or isomaltulose is critical to meet the commercial value due to insufficient production of enzymes as biocatalysts. Thus mass production of sucrose isomerase and optimized bioconversion and downstream process is essential to make predominant product of trehulose and/or isomaltulose. Therefore heterologus expression of such enzymes is extremely desired to design a cost effective and much safe bioconversion process. Heterologus expression of gene products in different expression system is sometimes limited by the presence of codons that are infrequently used in other organisms. Expression of such genes can be enhanced by systematic substitution of the endogenous codons with codons over represented in highly expressed prokaryotic genes. Redesigning a naturally occurring gene sequence by choosing different codons without necessarily altering the encoded amino acid sequence often dramatically increased protein expression levels. One disadvantage in biocatalyst used in production of low caloric sugar such as isomaltulose or trehalulose are the production cost of the enzyme due to low expression level of enzymes in native or heterologus organisms which remains quite challenging.

Although number of microorganisms such as *Protaminobacter rubrum, Serratia plymuthica, Erwinia rhaponiciti, Pseudomonas mesoacidophila* and *Agrobacterium raadiobacter* have been recognized for their ability to produce sucrose isomerase to convert sucrose in to isomaltulose and/or trehalulose at different ratios in given reaction conditions. However the mass production of pure isomaltulose and/or trehalulose is critical to meet the commercial value due to insufficient production of enzyme as biocatalysts.

Even though the enzymes are known that are capable of catalyzing the rare sugars but the gap still remain in mass production of enzymes and difficulties in their expression levels.

The inventors has identified the production constrain of rare disaccharides which is a bottleneck for industrial scaling up and identified the expression level in heterologous is low for certain nucleotide which are less preferred. In order to overcome such problem, the nucleotide sequence obtained from *Pseudomonas mesoacidophila* MX45 and *Pantoea dispersa* UQ68J, encoding for the enzymes responsible for bio-conversion were modified to increase the expression level substantially. Such modification resulted in better expression of the enzymes sucrose isomerase of *Pseudomonas mesoacidophila* MX45 and isomaltulose synthase of *Pantoea dispersa* UQ68J in *E. coli*. The *E. coli* host organism used in the invention is JM109 (a K-12 *E. coli* strain) was used for heterologus expression of recombinant Sucrose isomerase and isomaltulose synthase. It has been shown the *E. coli* K-12 cannot be converted into an epidemic pathogen by laboratory manipulation with r-DNA molecules and it will not colonize the human intestinal tract.

The present invention offers an alternative process for producing rare disaccharides, in which the enzymes were expressed in *E. coli* at a higher level by modifying the gene sequence. In other words, the present research has made and effort to genetically modify the gene responsible for the production of enzymes, namely sucrose isomerase and isomaltulose synthase to be used in bioconversion of sucrose in to trehalulose and isomaltulose, respectively. The genetic modification has resulted in increase in expression of protein in *E. coli* host.

SUMMARY OF THE INVENTION

Accordingly the present invention discloses a modified gene sequence encoding for sucrose isomerase (SIase) of *Pseudomonas mesoacidophila* MX45 responsible for conversion of sucrose in to trehalulose and optimized expression of SIase in *E. coli* for mass production of biocatalyst for bioconversion of sugars in an optimum conditions.

Further, invention discloses a modified gene sequence encoding for isomaltulose synthase (ISase) of *Pantoea dispersa* UQ68J responsible for conversion of sucrose in to isomaltulose and optimized expression of ISase in *E. coli* for mass production of biocatalyst for bioconversion of sugars in an optimum conditions.

The invention also discloses expression constructs comprising the modified genes to be expressed in *E. coli*.

The invention also relates to a process of producing trehalulose and isomaltulose from sucrose using the recombinant enzymes obtained from modified gene.

The inventors also found consistent conversion of sucrose in to trehalulose or isomaltulose by immobilized recombinant sucrose isomerase and isomaltulose synthases here in referred as SIase and ISase, respectively in contact with up to 60% sucrose in the reaction mixture. Moreover the 110 units of immobilized ISase were able to achieve maximum conversion of sucrose into isomaltulose within 6 to 10 hrs. at 30° C. In the prior art for similar kind of conversion of sucrose to isomaltulose, the time consumed was 48 hours (U.S. Pat. No. 4,640,894 and U.S. Pat. No. 5,336,617).

DETAILED DESCRIPTION OF THE INVENTION

The present invention discloses a modified gene sequence encoding for sucrose isomerase (SIase) of *Pseudomonas mesoacidophila* MX45, responsible for conversion of sucrose in to trehalulose and isomaltulose, and optimized expression of SIase in *E. coli* for mass production of biocatalyst for bioconversion of sugars in an optimum conditions.

The nucleotide sequence is also modified to increase the expression of isomaltulose synthase (ISase) of *Pantoea dispersa* UQ68J which is responsible for conversion of sucrose in to isomaltulose predominantly.

The invention also discloses expression constructs comprising the modified genes to be expressed in *E. coli*. The invention also relates to a process of producing trehalulose and isomaltulose from sucrose using the enzyme obtained from modified genes.

Upon comparing with the expression level of the native sucrose isomerase and isomaltulose synthase, it was found that the modification carried out in the native gene resulted in an increase in expression level in the range of 14% to 19% of the total cellular protein.

The present invention also discloses a novel and inventive protocol to assess the protein degradation and leaching during immobilization and bioconversion process using protein specific antibodies. Till date, no process has been shown to distinguish the whole length protein from degraded one. All available processes involve epitope tag to identify the whole length protein and therefore the degraded protein is not taken into consideration. For this process the recombinant proteins were expressed with 6×HIS epitope tag by using the pET23-SI and pET15-IS (FIGS. 1B and 2B) constructs and the recombinant proteins were purified by one step purification using an appropriate affinity matrix. The pure proteins were used as immunogen to generate polyclonal antibody in New Zealand white rabbits. The purified protein showed strong immunogenic response and anti sera were purified by affinity chromatography using Protein A-Sepharose 4B. Affinity purified antibody used in analytical process mentioned in the embodiment.

Gene encoding for sucrose isomerase was modified for enhanced expression in *Escherichia coli* was synthesized using gene modification. The modified gene sequence is represented as SEQ ID NO 1. Similar modification was done to increase the expression of isomaltulose synthase in *E. coli* is represented as SEQ ID NO 2. Both sequence ID NOs 1 and 2 were cloned in to pET11 using NdeI and BamHI restriction enzyme site to generate pET11-SI and pET11-IS constructs. Cloned gene sequences were confirmed by sequence analysis.

In a further aspect of the invention, a recombinant plasmid DNA (pET11-SI and pET1-IS) were transformed into *E. coli* expression host JM109 by electro transformation method to express sucrose isomerase and isomaltulose synthase, respectively. A stable transformants were selected and deposited in international depository, namely MTCC, Chandigarh bearing accession number MTCC5785 and MTCC5784 for sucrose isomerase and isomaltulose synthase, respectively.

In another embodiment of the invention, the large scale production of the above enzymes is disclosed. Importantly, the medium used for this purpose comprises no components of animal origin. The components of the medium were di-ammonium hydrogen phosphate, potassium dihydrogen phosphate and citric acid, which were sterilized in situ in the fermenter. Post sterilization a solution containing glucose, metal ions, trace elements and EDTA were added to the basal salt medium. Liquor ammonia was used as an alkali and nitrogen source. The temperature of the fermentation was maintained at 30 to 37° C. at a pH 5 to 8 and oxygen level was maintained not less than 40%, throughout the fermentation. The fermentation process at 2 L scale yields about 30-40 g/l biomass.

The organism containing the synthesized gene is able to produce more enzyme as a result of genetic modification of the native nucleic acid sequence of *Pseudomonas mesoacidophila* MX45 and *Pantoea dispersa* UQ68J. Besides the production of soluble enzyme, the inclusion bodies formed in the process is solubilized and refolded in vitro into active form using standard refolding conditions. In addition production of more soluble proteins in vivo were also achieved by co-expression of modified gene constructs (pET11-SI and pET11-IS) together with chaperone plasmids such as: pG-KJE8 or pGro7 or pKJE7 or pG-Tf2 or pTf16 (Takara).

Another aspect of the present invention is the immobilization of purified or partially purified enzymes in a suitable matrix known in the art for continuous operation.

In one more aspect of the invention relates to immobilization of the enzymes, namely, Slase and ISase using a suitable matrix. Protein retention was found to be about 70-80% (w/v).

The optimization of process parameters for the production of trehalulose and isomaltulose were carried out with varying pH and temperature, which were used for the production.

In one more feature of the invention is that the production of trehalulose from sucrose was carried out by using 25 to 100 units of immobilized Slase enzymes with varying amount of sucrose as a substrate. The conversion of sucrose to trehalulose reached saturation at higher substrate concentration of more than 50% (w/w) at enzyme concentration of 100 to 200 Units preferably 120 to 150 units of enzyme with a reaction time of about 8 hrs.

The sugar solution produced in the process passed through cation and anion exchange resins to remove salt and ions present in buffer solutions and concentrated by any known means, preferably using rotary vacuum evaporator to obtain 90% purity.

In one more feature of the invention is that the production of isomaltulose form sucrose was carried out by using 25 to 100 units of immobilized ISase enzymes with varying amount of sucrose as a substrate. The reaction was carried out with substrate concentration ranging from 10% to 60% at a temperature in the range of 10° to 50° C. and the pH in the range of 5 to 9. The conversion of sucrose to trehalulose reached saturation at higher substrate concentration of more than 50% (w/w) at enzyme concentration of 100 to 200 Units preferably 120 to 150 units of enzyme with a reaction time of about 8 hrs (Tables 3 and 4).

The isomaltulose sugar solution passed through cation and anion exchange resins to remove salt and ions present in buffer solutions till the time the traces removed. The sugar solution was concentrated using rotary vacuum evaporator system and subsequently passed through a column packed with activated charcoal, in order to remove the color. The purity of the product was analyzed by HPLC and was found to be about 83%.

BRIEF DESCRIPTION OF THE DRAWINGS

FIG. 1: Schematic view of a gene construct generated for expression of sucrose isomerase in *E. coli*
A: Sucrose isomerase (SI) was cloned into pET11a using NdeI and BamHI sites. Sucrose isomerase (SI) gene is flanked by BglII, XbaI and NdeI at 5' end, and BamHI at 3' end. During cloning procedure NheI site was removed. The properties of plasmid are: T7 promoter, T7 terminator and Ampicillin resistance marker.
B: Sucrose isomerase encoding sequence (SI) was cloned into pET23a using BamHI and HindIII sites. Sucrose isomerase (SI) gene is flanked by BglII, XbaI, NdeI, NheI and BamHI at 5' end, and HindIII, NotI and XhoI at 3' end. During cloning procedure EcoRI, SacI and SalI sites were removed. The properties of plasmid are: T7 promoter, T7 terminator, Epitope tag: 6×HIS and Ampicillin resistance marker.

FIG. 2: Schematic view of a gene construct generated for expression of isomaltulose synthase in *E. coli*
A: Isomaltulose synthase encoding sequence (IS) was cloned into pET11a using NdeI and BamHI sites. Isomaltulose synthase (IS) gene is flanked by BglII, XbaI and NdeI at 5' end, and BamHI at 3' end. During cloning procedure NheI site was removed. The properties of plasmid are: T7 promoter, T7 terminator and Ampicillin resistance marker.
B: Isomaltulose synthase encoding sequence (IS) was cloned into pET15b using NdeI and BamHI sites. Isomaltulose synthase (IS) gene is flanked by NcoI and NdeI at 5' end and HindIII at 3' end. During cloning procedure XhoI site was removed. The properties of plasmid are: T7 promoter, T7 terminator, Epitope tag: 6×HIS and Ampicillin resistance marker.

FIG. 3: Expression analysis of recombinant sucrose isomerase in *E. coli*.
A. Control and recombinant *E. coli* cells [JM109 carrying pET11-SI] were induced for protein expression by addition of 0.5 mM IPTG into media. Cells were lysed and supernatant and pellet fractions were subjected to 10% SDS-PAGE. Control strain: Lane 1 and 2 are uninduced and induced total cell lysate. Recombinant strain: Lane 3 and 4 are uninduced and induced total cell lysate. Cell fractions of recombinant strains: Lane 6 and 7 are uninduced cell supernatant and pellet, Lane 8 and 9 are two hrs induced supernatant and pellet, Lane 10 and 11 are four hrs induced supernatant and pellet. Abbreviations are: M: Protein molecular weight marker and kDa=Kilo Dalton.
B. Identity analysis of recombinant protein by Western blot analysis. Lane 1 and 2: Host cell lysate un-induced and induced. Lane 3 and 4: Recombinant strain un-induced and induced. Immuno-detection was carried our using protein specific antibodies.

FIG. 4: Expression analysis of recombinant isomaltulose synthase in *E. coli*.
A. Control and recombinant *E. coli* cells [JM109 carrying pET11-IS] were induced for protein expression by addition of 0.5 mM IPTG into media. Cells were lysed and supernatant and pellet fractions were subjected to 10% SDS-PAGE. Control strain: Lane 1 and 2 are uninduced and induced total cell lysate. Recombinant strain: Lane 3 and 4 are uninduced and induced total cell lysate. Cell fractions of recombinant strains: Lane 6 and 7 are uninduced cell supernatant and pellet, Lane 8 and 9 are two hrs induced supernatant and pellet. Abbreviations are: M: Protein molecular weight marker and kDa=Kilo Dalton.
B. Identity analysis of recombinant protein by Western blot analysis. Lane 1 and 2: Host cell lysate un-induced and induced. Lane 3 and 4: Recombinant strain un-induced and induced. Immuno-detection was carried our using protein specific antibodies.

FIG. 5: HPLC analysis of recombinant sucrose isomerase activity for substrate to product conversion.
The reaction mixtures were subjected to HPLC analysis to confirm the residual substrate and product formation. The product peaks were confirmed with commercially available sucrose and isomaltulose, trehalulose as substrate and product standards, respectively.

FIG. 6: HPLC analysis of recombinant isomaltulsoe synthase activity for substrate to product conversion.
The reaction mixtures were subject to HPLC analysis to confirm the residual substrate and product formation. The product peaks were confirmed with commercially available Sucrose and isomaltulose as substrate and product standards, respectively.

FIG. 7: Analysis of purified Slase
A. Different fractions and purified protein were separated on 12% SDS-PAGE and stained by coomassie brilliant blue R250. Loading pattern are Lane 1: Marker; Lane 2: Total cell Lysate; Lane 3: Cell lysate before loading in column 1; Lane 4: Column 1 purified Slase; Lane 5: Column 2 purified Slase.
B. Identity analysis of purified recombinant protein by Western blot analysis. Lane 1: Marker; Lane 2: Total cell Lysate; Lane 3: Cell lysate before loading in column 1; Lane 4: Column 1 purified Slase; Lane 5: Column 2 purified Slase. Immuno-detection was carried our using protein specific antibodies.

FIG. 8: Analysis of purified ISase
A. Different fractions and purified protein were separated on 12% SDS-PAGE and stained by coomassie brilliant blue R250. Lane 1: Molecular weight marker, Lane 2 to 6: Fractions 1 to 7, Lane 9: Crude cell lysate.
B. Identity analysis of purified recombinant protein by Western blot analysis. Lane 1: Total cell Lysate, Lane 2 and 3: Supernatant and Cell lysate of recombinant cell lysate, Lane 4: Purified ISase. Immuno-detection was carried our using protein specific antibodies.

FIG. 9: Activity of a sucrose isomerase against reaction pH and reaction temperature. The reaction mixture containing sucrose and purified Slase were incubated at different pH and temperature as indicated. Bioconversion reaction stopped by boiling the reaction mixture at 95° C. HPLC analysis of the reaction mixture confirmed the residual substrate and product formation. The product peaks were confirmed with commercially available sucrose and isomaltulose, trehalulose as substrate and product standards FIG. 10: Activity of an isomaltulose synthase against reaction pH and reaction temperature. The reaction mixture containing sucrose and purified ISase were incubated at different pH and temperature(s) as indicated. The bioconversion the reaction stopped by boiling the reaction mixture at 95° C. HPLC analysis confirmed the residual substrate and product formation. The product peaks were confirmed with commercially available sucrose and isomaltulose as substrate and product standards FIG. 11: Sequence alignment analysis of modified gene sequence with native gene sequence encoding for sucrose isomerase.
Modified gene sequence (represented as "modified") (SEQ ID NO: 1) was subjected to sequence alignment with native gene sequence (represented as "native") (SEQ ID NO:3) of *Pseudomonas* mesoacidophila MX45 using multiple sequence alignment tool (ClustalW2). The nucleotides of modified gene sequence were marked as (.) and homology shared to native sequence was marked as (*). In the modified gene 22% of nucleotides were changed and compared to native gene sequence, in addition 66 nucleotides (22 codons) were removed after ATG start codon which codes for 22 amino acid predicted signal sequence in *P. mesoacidophila* MAX-45.

FIG. 12: Sequence alignment analysis of modified gene sequence with native gene sequence encoding for isomaltulose synthase.
Modified gene sequence (represented as "modified") (SEQ ID NO:2) was subjected to sequence alignment with native gene sequence (represented as "native") (SEQ ID NO:4) of *Pantoea dispersa* UQ68J using multiple sequence alignment tool (ClustalW2). The nucleotides of modified gene sequence were marked as (.) and homology shared to native sequence was marked as (*). In the modified gene 20% of nucleotides were changed and compared to native gene sequence, in addition 96 nucleotides (32 codons) were removed after ATG start codon which codes for 22 amino acid predicted signal sequence in *Pantoea dispersa* UQ68J.

EXAMPLES

The following examples are given by way of illustration, which should not be construed to limit the scope of the invention.

Example 1

Gene Construction

Gene encoding for sucrose isomerase (SI) was modified for enhanced expression in *Escherichia coli* was synthesized using gene synthesis approach. The modified gene sequence is represented as SEQ ID NO 1. Similar modification was done to increase the expression of isomaltulose synthase in *E. coli* as represented in SEQ ID NO 2. Both sequence ID NOs 1 and 2 were cloned in to pUC57 using EcoRV restriction enzyme site to generate pUC57-SI and pUC57-IS constructs. Cloned gene sequence was confirmed by sequence analysis.

The DNA fragment encoding for sucrose isomerase was PCR amplified using gene specific primers, and sub cloned into pET11a using NdeI and BamHI restriction enzyme sites to generate pET11-SI (FIG. 1A). In addition the coding region was PCR amplified without stop codon using gene specific primers and sub cloned into *E. coli* expression vector pET23a (FIG. 1B) using BamHI and HindIII restriction enzymes to generate pET23-SI-HIS construct expressing sucrose isomerase with C-terminal 6× Histidine tag. The recombinant plasmid carrying sucrose isomerase gene (pET11-SI and pET23-SI) was confirmed by restriction digestion analysis and followed by DNA sequencing.

The DNA fragment encoding for isomaltulose synthase was PCR amplified using gene specific primers, and sub cloned into pET11a using NdeI and BamHI restriction enzyme sites to generate pET11-IS (FIG. 2A). In addition the coding region was PCR amplified without stop codon using gene specific primers and sub cloned into *E. coli* expression vector pET15b (FIG. 2B) using NdeI and HindIII restriction enzymes to generate pET15-IS-HIS construct expressing isomaltulose synthase with C-terminal 6× Histidine tag. The recombinant plasmid carrying isomaltulose synthase gene (pET11-IS and pET15-IS) was confirmed by restriction digestion analysis and followed by DNA sequencing.

Example 2

Development of Recombinant *E. coli* with Gene Constructs For Sucrose Isomerase

Recombinant plasmid DNA (pET11-SI) was transformed into *E. coli* expression host JM109 by electro transformation method and grown on Luria-Bertani (LB) agar plates containing ampicillin (50 g/ml). Individual colonies were picked and grown on LB liquid or defined media containing ampicillin (75 g/ml) for overnight at 37° C. Overnight culture was re-inoculated into 0.1 $OD_{600}$ in LB liquid or defined media without ampicillin and grown up to 0.6 $OD_{600}$ and the cells were induced for protein expression by addition of 0.5 mM of IPTG (Isopropyl β-D-1-thiogalactopyranoside) and incubated at 37° C. An aliquot of E. coli culture was collected at different time points. The cell lysate was subjected to SDS-PAGE and Western blot analysis to verify the protein expression (FIG. 3).

For Isomaltulose Synthase

Recombinant plasmid DNA (pET11-IS) was transformed into E. coli expression host JM109 by electro transformation method and grown on Luria-Bertani (LB) agar plates containing ampicillin (50 g/ml). Individual colonies were picked and grown on LB liquid or defined media containing ampicillin (75 g/ml) for overnight at 37° C. Overnight culture was re-inoculated into 0.1 $OD_{600}$ in LB liquid or defined media without ampicillin and grown up to 0.6 $OD_{600}$ and the cells were induced for protein expression by addition of 0.5 mM of IPTG (Isopropyl β-D-1-thiogalactopyranoside) and incubated at 37° C. An aliquot of E. coli culture was collected at different time points. The cell lysate was subjected to SDS-PAGE and Western blot analysis to verify the protein expression (FIG. 4).

Example 3

Production of Enzymes, Namely, Sucrose Isomerase and Isomaltulose Synthase

For large scale production of the above enzymes same protocols were followed. The medium used comprises no components of animal origin. The components of the medium were 4.0 g/L di-ammonium hydrogen phosphate, 13.3 g/L potassium dihydrogen phosphate and 1.7 g/L citric acid, 28 g/L glucose, 1.2 g/L MgSo4.7H2O, 45 mg/L Thiamine HCL, 1 g/L CoCl2.6H2O, 6 g/L MnCl2.4H2O, 0.9 g/L CuSo4.5H2O, 1.2 g/L H3BO3, 0.9 g/L NaMoO4, 13.52 g/L Zn (CH3COO—), 40 g/L Fe-Citrate and 14.1 g/L EDTA. Liquor ammonia was used as an alkali and nitrogen source. The temperature of the fermentation was maintained at 37° C. at a pH 6.9 and oxygen level was maintained not less than 40%, throughout the fermentation. The fermentation process at 2 L scale yields 30-40 g/l biomass.

Example 4

Purification of Enzymes

After completion of the fermentation the cells were centrifuged at 5000 g for 10 min and resuspend in 20 mM Tris-EDTA (TE) buffer, pH 8.0. The cells were lysed using the cell disruptor at 25 KPsi twice and the resulted cell lysate was clarified by centrifugation. The crude cell-free extract obtained from the supernatant following centrifugation at 27 000 g for 30 min at 4° C. was used for the purification. Clarified crude cell lysate was applied onto a Q-Sepharose column (GE, Healthcare) pre-equilibrated with 20 mM Tris-HCl buffer pH 8.0 and washed with five column volume of same buffer containing 100 mM NaCl. The bound proteins were eluted with NaCl gradient (0.1-0.4 M) in the same buffer, followed by step elution with 0.5 M and 1M NaCl wash in the same buffer. Fractions were collected and tested for sucrose isomerase and isomaltulose synthase activity and purity by SDS-PAGE (FIGS. 7 and 8). The purification yield, activity recovery and fold purification for sucrose isomerase and isomaltulose synthase were shown in Table 1 and Table 2, respectively. Fractions containing the purified protein were dialyzed against 20 mM Tris pH 8.0 for 16 hours at 4° C. and concentrated by ultrafiltration using Centricon YM-10 devices (Millipore) prior to immobilization or stored with 20% glycerol at −20° C.

TABLE 1

Purification table for Sucrose isomerase

| S. No | Sample | Volume (ml) | Protein (mg/ml) | Total Protein (mg) | IU/mg | Total Activity (IU) | Protein Yeild (%) | Fold Purification | Activity Recovery (%) |
| --- | --- | --- | --- | --- | --- | --- | --- | --- | --- |
| 1 | Crude | 50 | 45.13 | 2256.5 | 46.94 | 105920 | 100 | 1 | 100 |
| 2 | Loading | 63 | 30.4 | 1915.2 | 55.15 | 105623 | 84.8 | 1.1 | 99.7 |
| 3 | Purified | 112 | 1.54 | 172.35 | 550 | 947.92 | 8.99 | 9.97 | 89.5 |

TABLE 2

Purification table for isomaitulose synthase

| Steps | Sample | Volume (ml) | Protein (mg/ml) | Total protein (mg) | Specfic activity (IU/mg) | Total activity (IU) | Protein yield (%) | Fold of purification | Activity recovery (%) |
| --- | --- | --- | --- | --- | --- | --- | --- | --- | --- |
| Cell lysate Purification | Loading | 60 | 7.443 | 446.57 | 397.3 | 177425 | 100 | 1 | 100 |
| | Pooled fractions | 85 | 4.204 | 357.26 | 442 | 157908 | 80 | 1.25 | 89 |

Example 5

Immobilization of Enzymes

The same protocol was followed for Slase and ISase. Partially purified or purified Slase and ISase were dialyzed against 20 mM Tris buffer (pH 8.0) for 16 hours at 4° C. followed by mixing with equal volume of 4% sodium alginate (final concentration of sodium alginate was 2% w/v). The Slase or ISase containing sodium alginate solution was dropped by a surgical needle into chilled 0.2 M $CaCl_2$ solution with constant stirring. Immobilized beads were kept in $CaCl_2$ overnight at 4° C., followed by water wash and kept on a blotting paper for drying at 4° C. Protein retention was found to be 85% w/v with 2% w/v of sodium alginate.

Example 6

Production of Rare Disaccharides
Production of Trehalulose by Recombinant Slase

The optimization of process parameters for the production of trehalulose was carried out with varying pH and temperature, which were used for the production of trehalulose. Results are shown in FIG. 9.

Production of trehalulose form sucrose was carried out by using 110 units of immobilized SI enzymes with 10%, 20%, 30% and 40% sucrose solution in 20 mM Sodium Acetate, 10 mM $CaCl_2$ buffer pH 6.5 at 14° C.

The sugar solution was subjected to cation and anion exchange resins to remove salt and ions present in buffer solutions.

The sugar solution was concentrated using rotary vacuum evaporator system and subsequently passed through a column packed with activated charcoal, in order to remove the color. The purity of the product was analyzed by HPLC (FIG. 5) and ions contaminations were analyzed in ion chromatography (Dionex). Physico-chemical properties and purity of the product were carried out using standard techniques to confirm the safety aspects of produced trehalulose in this process. Bioconversion of trehalulose from sucrose was observed to be ~92%.

TABLE 3

Production of trehalose by immobilized recombinant sucrose isomerase

| Substrate (%) | Immobilized enzyme (U) | trehalulose:isomaltulose:sucrose ratio after 6 hours of bioconversion |
|---|---|---|
| 10 | 110 | 92:08:00 |
| 20 | 110 | 88:06:06 |
| 30 | 110 | 83:03:14 |
| 40 | 110 | 76:02:22 |
| 50 | 110 | 55:00:45 |

Production of Isomaltulose by Recombinant ISase

The optimization of process parameters for the production of isomaltulose was carried out with varying pH and temperature, which were used for the production isomaltulose. Results are shown in FIG. 10.

Production of isomaltulose from sucrose was carried out by using 110 units of immobilized ISase with 100 g/l, 200 g/l and 400 g/l sucrose solution was used in 20 mM Tris buffer, 5 mM $MnCl_2$ (pH 8.0) at 35° C.

The sugar solution was subjected to cation and anion exchange resins to remove salt and ions present in buffer solutions.

The sugar solution was concentrated using rotary vacuum evaporator system and subsequently passed through a column packed with activated charcoal, in order to remove the color. The purity of the product was analyzed by HPLC (FIG. 6) and ions contaminations were analyzed in ion chromatography (Dionex). Physico-chemical properties and purity of the product were carried out using standard techniques to confirm the safety aspects of produced isomaltulose in this process. Bioconversion of isomaltulose form sucrose was observed ~83%.

TABLE 4

Production of isomaltulose by immobilized recombinant isomaltulose synthase

| Substrate (%) | Immobilized enzyme (U) | Isomaltulose:trehalulose:sucrose/glucose/fructose ratio after 14 hours of bioconversion |
|---|---|---|
| 10 | 140 | 91.5:1.5:7.0 |
| 20 | 140 | 90.0:1.2:8.8 |
| 30 | 140 | 87.0:0.6:12.4 |
| 40 | 140 | 83.0:00:17.0 |
| 50 | 140 | 60.0:00:40.0 |

ADVANTAGE OF THE INVENTION

The genetically modified genes encoding for sucrose isomerase and isomaltulose synthase is capable of expressing 14% to 19% more of the total cellular protein as compared to native gene.

The enzyme produced by the present process appears to be more active as the enzyme requirement and time required for sugar conversion substantially lower than the native enzymes.

NON-PATENTED LITERATURE

Nagai, Y. T., Sugitani, and K. Tsuyuki. 1994, Characterization of alpha-glucosyltransferase from Pseudomonals mesoacidophila producting trehalulose. Biosci. Biotechnol. Biochem. 58:1789-1793.

Watzlawick, H., Mattes, R. 2009. Gene cloning, protein characterization, and alteration of product selectivity for the trehalulose hydrolase and trehalulose synthase from "Pseudomonas mesoacidophila" MX-45. Appl. Environ. Microbiol. 75:7026-7036.

Wu, L., Birch, R. G. 2004. Characterization of *Pantoea dispersa* UQ68J: producer of a highly efficient sucrose isomerase for isomaltulose biosynthesis. J. Appl. Microbiol. 97: 93-103.

The invention claimed is:

1. A modified polynucleotide encoding an isomaltulose synthase, wherein the modified polynucleotide comprises the nucleotide sequence of SEQ ID NO: 2.

2. An expression construct comprising the modified polynucleotide according to claim 1.

3. The expression construct according to claim 2, wherein the modified polynucleotide is operably linked to a T7 promoter.

4. An isolated host cell comprising the expression construct of claim 2.

5. The host cell of claim 4, wherein the host cell is a prokaryotic host cell.

6. A process for production of an isomaltulose synthase, said process comprising the steps of:
   1. culturing the host cell of claim 4 in a suitable medium in presence of IPTG or lactose for 2-3 hours to produce the isomaltulose synthase,
   2. isolating the isomaltulose synthase from the host cell, and
   3. purifying the isomaltulose synthase using chromatographic techniques.

7. A process for the production of isomaltulose from sucrose, said process comprising the steps of:
   1. culturing the host cell of claim 4 in a suitable medium in presence of IPTG or lactose for 2-3 hours to produce the isomaltulose synthase,
   2. isolating the isomaltulose synthase from the host cell, and purifying the isomaltulose synthase using chromatographic techniques,
   3. immobilizing the purified isomaltulose synthase in a suitable matrix, and
   4. contacting sucrose with the immobilized isomaltulose synthase for a period in the range of 4 to 14 hours to produce isomaltulose.

8. The process of claim 7, wherein 91% of total sugar produced is isomaltulose.

9. The process according to claim 6, wherein the host cell is a prokaryotic host cell.

10. The process according to claim 9, wherein the host cell is an *Escherichia coli* cell.

* * * * *

SEQUENCE LISTING

```
<160> NUMBER OF SEQ ID NOS: 4

<210> SEQ ID NO 1
<211> LENGTH: 1686
<212> TYPE: DNA
<213> ORGANISM: Artificial Sequence
<220> FEATURE:
<223> OTHER INFORMATION: Synthetic oligonucleotide

<400> SEQUENCE: 1
atggaagaag  ccgtcaaacc  gggtgctccg  tggtggaaat  ccgcagtgtt  ttatcaagtc        60
```

```
tatccgcgtt cattcaaaga tacgaatggt gatggcattg gtgattttaa aggtctgacc      120
gaaaaactgg attatctgaa aggcctgggt atcgatgcca tttggatcaa cccgcattac      180
gcatctccga acacggataa tggctatgat attagtgatt accgcgaagt tatgaaagaa      240
tatggtacca tggaagattt cgatcgtctg atggcggaac tgaaaaaacg tggcatgcgc      300
ctgatggtgg atgtggttat caaccatagc tctgatcagc acgaatggtt taaaagtagc      360
cgcgccagca agataatcc gtatcgtgat tattacttct ggcgcgatgg caaagatggt       420
catgaaccga caattaccc gagcttttc ggcggtagcg cgtgggaaaa agatccggtg        480
acgggccagt attacctgca ctattttggt cgccagcagc cggatctgaa ctgggatacc      540
ccgaaactgc gcgaagaact gtacgccatg ctgcgttttt ggctggataa aggcgttagt     600
ggtatgcgtt cgatacggt ggcaacctat agcaaaacgc cgggcttcc ggatctgacc        660 ccggaacaga tgaaaaactt cgccgaagca tatacccagg tccgaatct gcatcgttac       720 ctgcaggaaa tgcatgaaaa agtttcgat cactacgatg ccgtgaccgc aggcaaattt      780
ttggtgcgcc gctgaatcag gttccgctgt tcatcgatag ccgtcgcaaa gaactggata    840
tggcgtttac cttcgatctg attcgttatg atcgcgccct ggatcgttgg caccgatccc     900
gcgcaccctg gcagattttc gtcagacgat tgataaagtg gatgcgatcg ccggcgaata     960
cggttggaac accttttttcc tgggcaacca tgataatccg cgccgcgtttt ctcacttcgg   1020 tgatgatcgt ccgcagtggc gcgaagcaag tgcgaaagcc ctggcaaccg tgacgctgac   1080
ccagcgtggt accccgttta ttttccaggg cgatgaactg gtatgacga attatccgtt     1140 taaaaccctg caggatttcg atgatatcga agttaaaggc tttttccagg attacgtgga   1200
aacgggtaaa gcgaccgccg aagaactgct gacgaacgtt gcactgacca gccgtgataa   1260
tgcgcgcacc ccgtttcagt gggatgattc tgcaaatgcg ggcttcacca cgggtaaacc   1320
gtggctgaaa gttaacccga attataccga aattaacgcg gcccgcgaaa tcgcgatccg   1380
aaatctgtgt atagttttta ccgcaatctg attagcatcc gtcatgaaac gccggcactg   1440
agcaccggtt cttatcgtga tattgatccg agcaacgcgg atgtgtatgc ctacacgcgt   1500
tctcaggatg gtgaaaccta cctggtggtt gtgaatttta aagcagaacc gcgtagcttc   1560
acgctgccgg atggcatgca cattgcggaa accctgatcg aatctagtag cccggcagcg   1620
ccggcggctg gtgcggcttc gctggaactg caaccgtggc aaagtggtat ttacaaagtg   1680
aaataa                                                                1686
```

<210> SEQ ID NO 2
<211> LENGTH: 1701
<212> TYPE: DNA
<213> ORGANISM: Artificial Sequence
<220> FEATURE:
<223> OTHER INFORMATION: Synthetic oligonucleotide

<400> SEQUENCE: 2

```
atggcgacga acattcagaa agcgcagac ttcccgattt ggtggaaaca agcagtgttt       60
tatcagattt acccgcgttc attcaaagat agcaacggcg acggtatcgg cgatattccg      120
ggtatcatcg aaaaactgga ctacctgaaa atgctgggcg ttgatgccat ttggatcaat      180
ccgcattacg aatcaccgaa cacggataat ggttatgata tctcggacta ccgtaaaatt      240
atgaaagaat atggcagtat ggccgatttt gaccgcctgg tcgcagaaat gaacaaacgc      300
ggtatgcgtc tgatgattga catcgttatt aatcataccct ccgatcgcca ccgttggttc     360
```

```
gtccagagtc gttccggcaa agacaacccg tatcgtgatt attactttg gcgcgatggt      420 aaacagggcc aagctccgaa caattacccg agcttttcg gcggttccgc gtggcagctg      480
gacaaacaga ccgatcaata ttacctgcac tatttcgctc cgcagcaacc ggacctgaac      540
tgggataatc cgaaagttcg tgcggaactg tacgacatcc tgcgcttttg gctggataaa      600
ggtgtcagtg gcctgcgttt tgataccgtg gccacgttca gtaaaattcc gggttttccg      660
gatctgtcca agcacagct gaaaaacttt gcagaagcgt atacggaagg cccgaacatc      720
cataaataca tccacgaaat gaaccgccag gttctgagca atataatgt cgcgaccgcc      780 ggtgaaatct tcggcgtgcc ggtttctgcc atgccggatt actttgaccg tcgccgtgaa      840
gaactgaaca tcgcatttac cttcgatctg attcgcctgg accgttatcc ggatcagcgt      900
tggcgccgta accgtggac gctgagccag ttccgtcaag tcatttctca aaccgatcgc      960
gcggccggtg aatttggctg gaatgcgttt ttcctggata ccatgacaa tccgcgtcag     1020 gtgtcacact ttggtgatga ctcgccgcaa tggcgcgaac gtagcgcaaa agctctggca     1080
accctgctgc tgacgcagcg tgctacccg tttattttcc agggtgcgga actgggcatg     1140
acgaactacc cgttcaaaaa catcgaagaa ttcgatgaca tcgaagtgaa aggtttctgg     1200
aacgattacg tcgcatcagg caaagtgaat gcagctgaat ttctgcagga agtgcgcatg     1260
acgagccgtg acaactctcg caccccgatg cagtggaacg attcggttaa tgcgggtttc     1320
acccaaggca aaccgtggtt tcatctgaac ccgaattata aacagattaa cgcggcccgc     1380
gaagtgaata accggattc agttttctcg tattaccgtc agctgatcaa tctgcgccac     1440
caaattccgg ctctgacgtc aggcgaatat cgtgatctgg acccgcagaa caatcaagtt     1500
tatgcctaca cccgcatcct ggataacgaa aaatacctgg tggttgtcaa cttcaaaccg     1560
gaacagctgc attacgccct gccggataac ctgaccattg caagtctctct gctggaaaat     1620 gtgcaccagc cgtctctgca agaaaacgcc tctacgctga ccctggcacc gtggcaagct     1680
ggcatttaca aactgaatta a                                              1701

<210> SEQ ID NO 3
<211> LENGTH: 1755
<212> TYPE: DNA
<213> ORGANISM: Artificial Sequence
<220> FEATURE:
<223> OTHER INFORMATION: Synthetic oligonucleotide

<400> SEQUENCE: 3
atgcttatga agagattatt cgccgcgtct ctgatgcttg cttttcaag cgtctcctct       60 gtgagggctg aggaggccgt aaagccgggc gcgccatggt ggaaaagtgc tgtcttctat      120
caggtctatc cgcgctcgtt caaggatacc aacggtgatg ggatcggcga tttcaaagga      180
ctgacggaga agctcgacta tctcaagggg ctcggcatag acgccatctg gatcaatcca      240
cattacgcgt ctcccaacac cgataatggc tacgatatca gcgactatcg agaggtcatg      300
aaggaatatg ggacgatgga ggacttcgat cgtctgatgg ctgagttgaa gaagcgcggc      360
atgcggctca tggttgatgt cgtgatcaac cattcgagtg accaacacga atggttcaag      420
agcagccggg cctccaaaga caatccctac cgtgactatt atttctggcg tgacggcaaa      480
gacggtcacg agccaaacaa ttacccttcc ttcttcggcg gttcggcatg ggagaaggac      540
cccgtaaccg gcaatatta cctgcattat ttcggtcgtc agcagccaga tctgaactgg      600
gacacgccga gcttcgcga ggaactctat gcgatgctgc ggttctggct cgacaagggc      660
gtatcaggca tgcggttcga tacggtggct acctactcga agacaccggg tttcccggat      720
```

```
ctgacaccgg agcagatgaa gaacttcgcg gaggcctata cccaggggcc gaaccttcat    780
cgttacctgc aggaaatgca cgagaaggtc ttcgatcatt atgacgcggt cacggccggc    840
gaaatcttcg gcgctccgct caatcaagtg ccgctgttca tcgacagccg gaggaaagag    900
ctggatatgg ctttcacctt cgatctgatc cgttatgatc gcgcactgga tcgttggcat    960
accattccgc gtaccttagc ggacttccgt caaacgatcg ataaggtcga cgccatcgcg   1020
ggcgaatatg gctggaacac gttcttcctc ggcaatcacg acaatcccg tgcggtatcg    1080 cattttggtg acgatcggcc gcaatggcgc gaagcctcgg ccaaggctct ggccaccgtc   1140
accttgaccc agcgaggaac gccgttcatc ttccaaggag atgaactcgg aatgaccaac   1200
taccccttca agacgctgca ggactttgat gatatcgaag tcaaaggctt ctttcaggac   1260
tatgtcgaaa ccggaaaggc aactgccgag gaattgctga ccaatgtggc gttgactagc   1320
cgcgacaacg cccgcacgcc ctttcaatgg gatgacagtg ctaatgcggg attcacgacc   1380
ggcaagcctt ggctaaaggt caatccaaac tacactgaga tcaacgccgc gcgggaaatt   1440
ggcgatccta atcggtcta cagcttttac cgcaacctga tctcaatccg gcatgaaact   1500
cccgctcttt cgaccgggag ctatcgcgac atcgatccga gtaatgccga tgtctatgcc   1560
tatacgcgca gccaggatgg cgagacctat ctggtcgtag tcaacttcaa ggcagagcca   1620
aggagtttca cgcttccgga cggcatgcat attgccgaaa ccctgattga gagcagttcg   1680
ccagcagctc cggcggcggg ggctgcaagc cttgagctgc agccttggca gtccggcatc   1740
tacaaggtga agtaa                                                    1755

<210> SEQ ID NO 4
<211> LENGTH: 1797
<212> TYPE: DNA
<213> ORGANISM: Artificial Sequence
<220> FEATURE:
<223> OTHER INFORMATION: Synthetic oligonucleotide

<400> SEQUENCE: 4
atgtttctta atggatttaa gacagttatt gctctgacta tggcaagctc gtttttatctt    60 gccgccagcc cgttaactaa gccatcgacc cctattgccg caacgaatat acaaaagtcc   120
gctgattttc ccatttggtg gaaacaggca gtattttacc agatttatcc ccgctcattt   180
aaagatagca atggtgatgg tatcggcgat attcccggta tcattgagaa actggactat   240
ttaaaaatgc tgggagttga tgctatctgg ataaacccgc actatgagtc tcctaacacc   300
gacaatggtt acgatattag tgattatcgt aaaatcatga aggagtacgg cagcatggct   360
gactttgacc gtctggttgc cgaaatgaat aaacgtggta tgcgcctgat gattgatatt   420
gttatcaatc ataccagcga tcgtcaccgc tggtttgtgc agagccgttc aggtaaagat   480
aatccttacc gcgactatta tttctggcgt gatggtaaac agggacaggc tcccaataac   540
tatccctctt tctttggcgg ttcagcctgg caactgata aacagactga ccagtattat   600
ctgcactatt ttgcaccaca gcagccggat ctgaactggg ataacccaaa agttcgggct   660
gaactctacg atattctgcg tttctggctg gataaaggcg tatccggact acgttttgat   720
accgtggcta ctttctccaa aattcctggc ttcccggacc tgtcaaaagc gcagctgaag   780
aattttgccg aagcttatac tgaggggccg aatattcata aatatatcca tgaaatgaac   840
cgccaggtac tgtctaaata taatgttgcc accgctggtg aaatcttcgg tgtgccagtg   900
agtgctatgc cggattattt tgaccggcgg cgtgaagaac tcaatattgc tttcacctt    960
```

```
gatttgatca ggctcgatcg ttatcccgat cagcgctggc gtcgtaaacc atggacatta    1020
agccagtttc gtcaagttat ctctcagact gaccgtgccg ccggtgaatt tggctggaac    1080 gccttttttcc ttgataacca tgataacccg cgccaggtct cacactttgg tgacgacagc   1140
ccacaatggc gcgaacgctc ggcaaaagca ctggcaacgc tgctgctgac gcagcgtgcc    1200
acgccgttta tctttcaggg ggcggagttg ggaatgacta attaccccct taaaaatata    1260
gaggaatttg atgatattga ggttaaaggc ttctggaacg actatgtagc cagcggaaaa    1320
gtaaacgctg ctgaattttt acaggaggtt cgcatgacca gccgcgataa cagccgaaca    1380
ccaatgcagt ggaacgactc tgttaatgcc ggattcaccc agggcaaacc ctggtttcac    1440
ctcaatccca actataagca aatcaatgcc gccagggagg tgaataaacc cgactcggta    1500
ttcagttact accgtcaact gatcaacctg cgtcaccaga tcccggcact gaccagtggt    1560
gaataccgtg atctcgatcc gcagaataac caggtctatg cctatacccg tatactggat    1620
aatgaaaaat atctggtggt agttaatttt aaacctgagc agctgcatta cgctctgcca    1680
gataatctga ctattgccag cagtctgctg gaaaatgtcc accaaccatc actgcaagaa    1740
aatgcctcca cgctgactct tgctccgtgg caagccggga tctataagct gaactga      1797
```